United States Patent [19]

Holtkamp, Sr.

[11] Patent Number: Plant 6,436

[45] Date of Patent: Nov. 29, 1988

[54] AFRICAN VIOLET PLANT NAMED ROCKY MOUNTAIN

[76] Inventor: Reinhold Holtkamp, Sr., Werther Strasse 112, D4294 Isselburg, Fed. Rep. of Germany

[21] Appl. No.: 21,735

[22] Filed: Mar. 4, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Rocky Mountain characterized by its semi-double, mainly white flowers with purple red edges and centers; strong, upright flower stems that curve toward the center to form a bouquet above the leaves, profuse and long flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Rocky Mountain.

The new cultivar was referred to during the breeding and selection process by the designation H34/5, and is a product of a planned breeding program. The new cultivar was originated from a cross made by me in the controlled breeding program in Isselburg, Federal Republic of Germany. The female, or seed parent, was a cultivar designated 15/8-68 Red Single. The male, or pollen parent, was a cultivar designated GG4 Pink Star.

Rocky Mountain was discovered and selected by me in 1983 as a flowering plant within the progeny of the stated cross in a controlled environment in Isselburg, Federal Republic of Germany. Asexual reproduction of the new cultivar by leaf cuttings, as performed by me at Isselburg, Federal Republic of Germany, has demonstrated that the combination of characteristics, as herein disclosed for the new cultivar are firmly fixed and retained through successive generations of asexual reproduction.

Rocky Mountain has not been observed under all possible environmental conditions. The phenotype may vary significantly with such variations in environment as temperature, light intensity, and day length. The following observations, measurements, and values describe the new cultivar as shown in Isselburg, Federal Republic of Germany, and Nashville, Tenn., under greenhouse conditions which closely approximate those generally used in commercial practice.

The following traits have been repeatedly observed and are determined to be basic characteristics of Rocky Mountain, which, in combination, distinguish this African violet as a new and distinct cultivar:

(1) Strong, upright flower stems curving toward the center.

(2) First flash of flowers forms a tight bouquet above the leaves.

(3) Long blooming period.

(4) Profuse flowering on medium long stems (5.5–7.5 cm).

(5) Each plant carried up to 10–12 and more upright flower stems, each of which carries 7–9 flowers.

(6) Vigorous grower, compact habit.

(7) Plant saleable 9–10 weeks after potting.

(8) Medium dark green velvety leaves, slightly hairy.

(9) Long-lasting, non-dropping flowers.

(10) Seed capsule pushes slightly through.

(11) After maturity the flowers dry off and remain on the peduncle without being infected by botrytis.

(12) Semi-double flower, white with a purplish-red center as well as puplish-red margins around the petals.

(13) The flower has additional petals appearing within the center of the flower.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2:00 p.m. in Nashville, Tenn.

Botanical classification: *Saintpaulia ionantha,* Ramat., cv. Rocky Mountain.

Parentage:

*Male parent.*—GG4 Pink Star.

*Female parent.*—15/8-68 Red Single.

Propagation: The new cultivar holds its distinguishing characteristics through successive propagations by leaf cuttings.

Plant: From 7 cm to 9 cm tall when grown in pots, and approximately 27–29 cm in diameter when fully grown.

*Leaves.*—General form: heart-shaped. Diameter: 60–70 mm. Texture: soft and hairy. Aspect: velvety, slightly hairy, slightly frilled edges, surface somewhat like rolling hills. Veins: underside — well pronounced, light green, shiny. Color (upper side): green group 137B. Color (under side): green group 138D. Petiole: strong, upright, greenish, hairy.

*Flowers.*—Buds: ball-shaped, 7–8 mm before opening, generally partly greenish, partly purplish in color. Sepals: 5 spear-shaped, equally sized, large. Color: greenish-brown. Calyx: Shape: funnel-shaped. Aspect: spear-shaped, hairy. Peduncle: Length: 32–35 mm. Character: strong, upright, wire-like. Color: brownish. Individual flowers: Size: 32–35 mm in diameter. Shape: semi-double. Color (upper side): predominantly white, with edges and center 74A and darker. Color (underside): white diffused with 74C. Under cooler growing conditions and more intensive lighting, the purple red color became more intense. Borne: each flower stem carries 7–9 flowers on strong upright peduncles that are free-standing above the leaves. Corolla: slightly open flower head, free-standing above the leaves. Flowering habit: flowers 9–10 weeks after potting. The flower head is slightly open and free-standing above the leaves.

*Reproductive organs.*—Stamens: 2. Anthers: 2 filaments with 4 anther cells. Filaments: 3–4 mm in length. Pollen Color: 5A. Styles: 6–7 mm, dark purple with a light green base.

*Roots.*—Normally developed, white when young, turning slightly brownish when older.

Disease resistance: Good.

General Observations: Rocky Mountain is a vigorous grower with attractive velvet medium dark green leaves. Out of the center, 10–12 and more strong flower stems appear that are bending toward the center. Each flower stem carries 7–9 and more semi-double, frilled flowers that are purplish-red on the outer edge and in the center. Some flower petals have a more intensive purplish-red color. The fully developed flower head has a compact habit, forming a nice bouquet. The leaves are slightly frilled on the edge, and the surface of the leaves is slightly undulating. At the point where the petiole attaches to the leaf, the two sides, left and right from the main vein, tend to angle upwards, forming a shallow, funnel-like appearance. Approximately 9–10 weeks after potting the plant is saleable. The flowers are long-lasting and non-dropping and the seed capsule pushes slightly through.

I claim:

1. A new and distinct cultivar of African violet named Rocky Mountain, as described and illustrated, and particularly characterized by its semi-double, mainly white flowers with purple red edges and centers; strong, upright flower stems that curve toward the center to form a bouquet above the leaves; profuse and long flowering, vigorous growth habit, flowering 9–10 weeks after potting, and its long-lasting and non-dropping flowers.

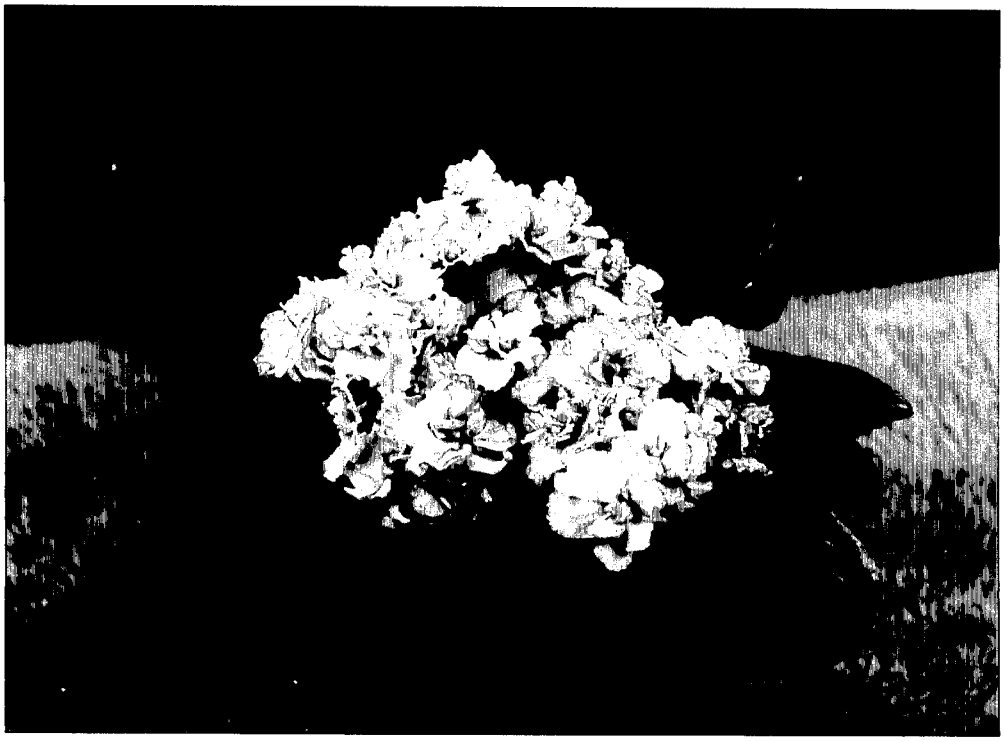

* * * * *